United States Patent [19]
Martin et al.

[11] Patent Number: 5,867,247
[45] Date of Patent: *Feb. 2, 1999

[54] APPARATUS AND METHOD FOR SIMULATION OF VISUAL DISABILITIES

[75] Inventors: Neil F. Martin, Potomac; Howard N. Robinson, Lutherville, both of Md.

[73] Assignee: Leonard Bloom, Towson, Md.; a part interest

[ * ] Notice: The term of this patent shall not extend beyond the expiration date of Pat. No. 5,495,305.

[21] Appl. No.: 865,001

[22] Filed: May 29, 1997

Related U.S. Application Data

[63] Continuation-in-part of Ser. No. 593,879, Jan. 30, 1996, which is a continuation-in-part of Ser. No. 593,880, Jan. 30, 1996, and a continuation-in-part of Ser. No. 331,029, Oct. 27, 1994, Pat. No. 5,495,305.

[51] Int. Cl.$^6$ .............................. G02C 7/10; G02C 7/04
[52] U.S. Cl. ...................... 351/177; 351/162; 351/163; 351/165
[58] Field of Search .......................... 351/160 R, 160 H, 351/161, 162, 163, 165, 177

[56] References Cited

U.S. PATENT DOCUMENTS 5,372,504  12/1994  Buechler .................................. 351/47

*Primary Examiner*—Scott J. Sugaman
*Attorney, Agent, or Firm*—Leonard Bloom

[57] ABSTRACT

Eyeglasses are modified to simulate ophthalmologic anomalies which may result from ophthalmic surgery. Various hazed eyeglass lenses are described.

4 Claims, 20 Drawing Sheets

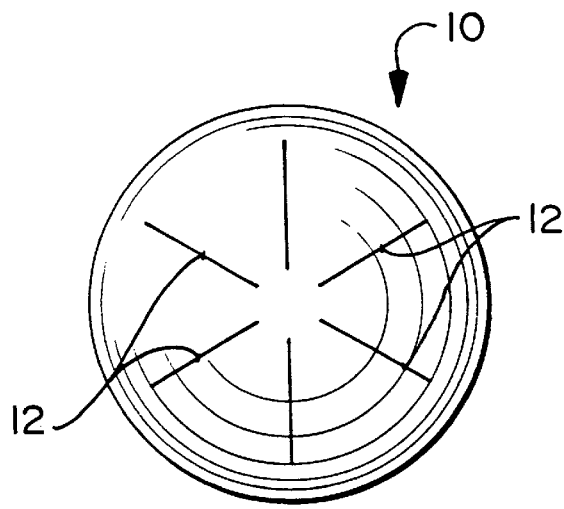 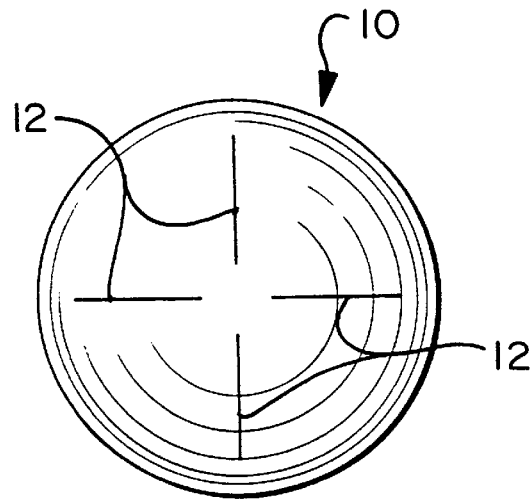
FIG. 4  FIG. 5
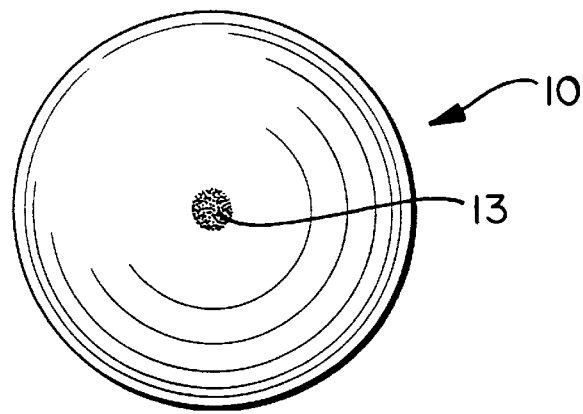
FIG. 6
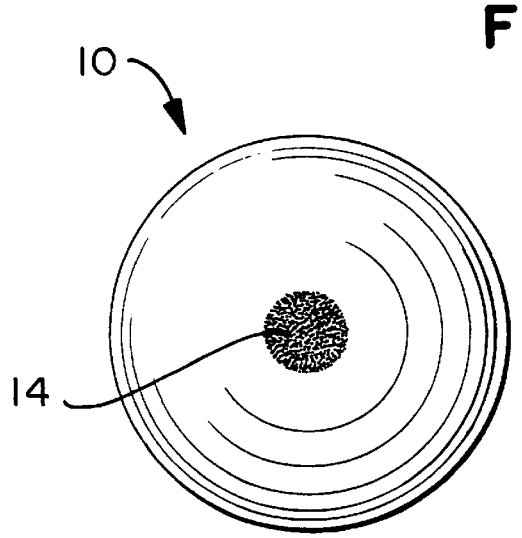 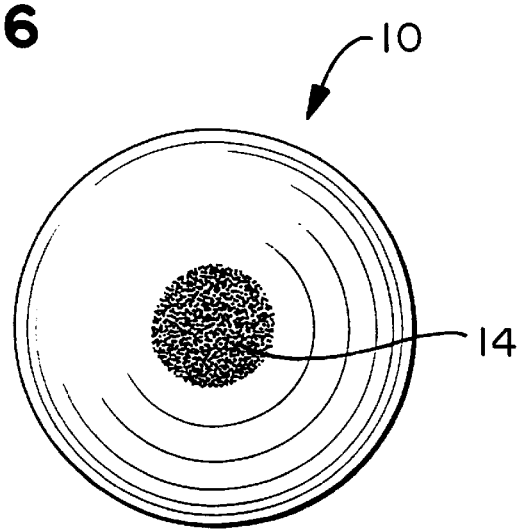
FIG. 7  FIG. 8

APPARATUS AND METHOD FOR SIMULATION OF VISUAL DISABILITIES

CROSS REFERENCE TO RELATED APPLICATIONS

This application is a continuation-in-part of our application, Ser. No. 08/593,879 and Ser. No. 08/593,880 both filed Jan. 30, 1996, which were continuations-in-part of our application Ser. No. 08/331,029 filed Oct. 27, 1994, now U.S. Pat. No. 5,495,305.

BACKGROUND OF THE INVENTION

Medical diseases of the eye—as well as eye surgery, such as refractive surgery—can create post-operative visual disturbances for the patient. Because of this post-operative risk of visual disturbance, informed consent from the patient to the doctor is essential. As part of the presently practiced method of informed consent required from the prospective patient prior to surgery, the doctor describes to the patient what visual anomalies to expect as a result of the surgery. This description is open to subjective interpretation by the patient, and in many instances the information conveyed to the patient by the doctor is inadequate and is misinterpreted by the patient.

Significant visual distortions may commonly occur with cataracts and macular degeneration which, respectively, are the leading causes of treatable and non-treatable blindness in the United States. These diseases affect millions of patients and the visual difficulties suffered by the patients are sometimes difficult for medical personnel and the families of patients to understand and to appreciate.

Additionally, new refractive procedures, radial keratotomy (RK) and its related surgery, astigmatic keratotomy (AK) and excimer laser photorefractive keratectomy (PRK), are being performed on growing numbers of patients. Radial keratotomy (RK) and excimer laser photokeratotomy (PRK) are the dominant surgeries for the correction of refractive errors of the eye. It is estimated that approximately 300,000 to 500,000 RK procedures were performed in the U.S., and 250,000 to 300,000 PRK procedures were performed world wide during the year 1993. These surgeries are performed to correct myopia (nearsightedness) and astigmatism. Alone, myopia affects at least thirty percent of the population of the U.S. and higher proportions of the population in Far Eastern countries. PRK is also undergoing clinical trials, and approximately one million myopes will undergo PRK yearly in the U.S. once the procedure is finally approved by the FDA. PRK also shows promise for the correction of hyperopia (farsightedness).

Other refractive procedures are undergoing development which may extend the applicability of refractive surgery. These procedures include intra-lamellar corneal rings, automated lamellar keratectomy (ALK), intrastromal photoablation and "flap and zap" (ALK combined with PRK). All of the foregoing refractive procedures have the potential for reducing visual acuity and/or creating optical aberrations. Obtaining good (and legal) preoperative informed consent from patients undergoing these procedures, especially where there is an increasing amount of advertising relating to such surgery, is necessary and important. This is so because there is potential for postoperative permanent visual degradation from glare and loss of contrast sensitivity. Unmet patient expectations can create disappointment and anger and can lead to malpractice suits, even when good post-operative results are obtained. The healing response may influence the shape of the cornea in ways that are not predictable on a case by case basis. Moreover, the healing process, after surgery generally tends to fill in the cornea with new collagen, reversing some of the effects of the surgery. This healing may result in an irregular front surface of the cornea, producing, at times, visual distortion.

SUMMARY OF THE INVENTION

The main purpose of the present invention is to simulate some of the visual problems which may be encountered in refractive surgery (especially, starbursting with RK and glare with PRK). This simulation of visual problems will enhance the level of patient education, and communication between doctor and patient, in obtaining legally sufficient informed consent. Since visual distortions IF are phenomena that are difficult to explain, the invention provides great benefit to the patient, as well as the doctor, since the patient can be objectively apprised of how the surgery could affect post-operative vision. The herein disclosed invention provides methods for the patient to effectively assess the result of prospective surgery, so that he or she might have a means of evaluation based on his or her own physiological response.

With all this in mind, the inventors have provided a series of modified contact lenses, which when worn by a patient will produce the type of postoperative visual distortions that could be expected in some cases as a result of surgery of various types of eye surgery. Having worn the lens or lenses, and having actually experienced the visual distortion that could be produced as a result of surgery, the patient can make an educated judgement and give informed consent to the doctor prior to having surgery performed on the eye or eyes. Since the patient has worn the lenses and experienced visual distortion, he or she is less likely to complain to the doctor about any post-operative visual anomaly.

In addition to being useful for providing informed consent, the lenses of this invention also have educational uses. The lenses simulating visual disturbances and disease have significant educational utility for medical students and nurses in the classroom, as well as for doctors in practice. The lenses can be used to educate families of patients with ocular disease regarding the patient's pre-operative visual distortions, as well as possible post-operative visual anomalies; all of this with a specific view of letting the families know what can be expected as a result of surgery. Besides postoperative anomalies, among the disease conditions that may be simulated by the lenses of this invention are the various manifestations of cataracts, corneal opacities, retinal detachments, possibly macular degeneration, as well as hemi- and quadrantanopias.

It should be possible to simulate visual fields defects from neuro-ophthalmic conditions of the visual pathways such as:
1. optic neuropathies (central scotoma (blind spot) or altitudinal defect (half of the vision obscured above or below a central horizontal meridian through fixation);
2. hemianopia (half of the vision obscured in both eyes together along a vertical meridian through fixation) either homonymous (same side in both eyes) or heteronomous (opposite sides for both eyes—either bitemporal or binasal).

Central scotomas would be simulated by an absolute central CL opacity just smaller than the pupil and field defects would be simulated by opacity covering a half or a quarter of the CL extending through the center of the CL and covering a significant area of the lens (larger than the pupil to perhaps the size of the cornea, 11 to 12 mm). Optically, one may find that central opacities that are larger than the pupil may still allow light to enter the eye as peripheral light rays striking the cornea are refracted toward the pupil by the convex surface of the cornea. Specified opacity and size of opacity relative to the pupil size may require some experimentation to determine the optimum lens modification and therefore need some leeway until actual CL(s) are manufactured and tried clinically on the patient. As a specific modification the opaque CL areas may be oriented by using CL(s) that are toric or are truncated or have a configuration that provides ballast.

As a special embodiment of this invention, eyeglasses (spectacles) are modified so that their lenses are constructed so as to have modifications similar to the modifications on the contact lenses.

An important embodiment of the present invention is a disposable soft contact lens with laser or molded marks. The lens may be made very thin to be worn under (or over) the patient's own contact lenses (piggy back style) or under the patient's eyeglasses. In a preferred embodiment of this invention, the patient's prescription contact lens may be used to make the etched or marked lens.

The invention herein described is most concerned with a method for obtaining informed consent from a patient prior to surgery by fitting the patient with a device, the field of vision of which has been modified to simulate the ophthalmologic anomaly which might be experienced by the patient as a result of said surgery. The modified device can be a contact lens, an eyeglass or a pair of eyeglasses.

Other significant embodiments of devices for simulating visual anomalies are envisioned by the inventors. Among the embodiments contemplated are clip-on lenses which would fit over the patient's glasses; alternative to the clip-on lenses, the lenses could be such as would slide behind the lenses of the patient's eyeglasses.

Another embodiment contemplated by the inventors is a modified thin transparent film that can be pressed onto the lenses of eyeglasses or spectacles. This modified thin transparent film press on has markings thereon, such that when the film is applied to a lens of eyeglasses, the markings thereon will create in the field of vision of the eyeglasses an ophthalmologic anomaly.

A still further embodiment embraces a hinged visor or loupes which would be fitted over eyeglasses and produce the visual anomaly.

The improved invention falls into two areas; the first concerns simulation of PRK with hazy areas on the spectacles, and the second concerns RK with radial cuts on the spectacles. Although the inventors' original embodiment of a PRK/RK simulation device was a contact lens with which they sought to anatomically simulate the size and density of scares after PRK/PK procedures. Using eyeglasses or a spectacle PRK/RK simulation device is much simpler.

An important embodiment of this invention involves eyeglasses which are either bifocal or trifocal lenses. Each of these bifocal or trifocal lenses have a separate area of vision modified to simulate differing degrees of hazing which may result from ophthalmic surgery such as RK or PRK. A patient wearing such glasses can look through each area of the lense and experience and compare different degrees of hazing. In this way the patient is better able to give informed consent to the doctor prior to surgery.

To simulate PRK the inventors have found that lens in which the entire lens has a mild frosting gives a subjective visual appearance that some PRK patients have reported during their post-operative period. The Cokin diffusion filters 1, 2 and 3 appear to give a reasonable approximation of mild, moderate and severe haze, glare and halo. An easy prototype can be made by simply making three pairs of spectacles cutting the plastic Cokin lenses to fit the frames of these glasses. The spectacle frame should be able to fit over a patient's own glasses.

Cheaper styrene-type of lens such as used for solar shields may allow one to make spectacles either by heating the surface or perhaps by spraying it with fixative such as the type of mat fixative used for preservation of drawings.

The improved invention allows for the concept of a progressive diffusion filter. This diffusion filter could be used with trifocal, bifocal or multifocal lenses with discrete jumps or gradual progressive lens modifications. For example, the top area of the lens could have severe hazing and the bottom area of the lens could have mild hazing. This allows for one pair of lenses show all degrees of potential post-operative glare or halo-effect.

In addition, one could also use a progressive style lens to simulate over- and undercorrection with a plano center and, for example, a ±1 or 2-diopter lens above and below the central lens. This may be accomplished in a discreet multifocal fashion or in a progressive lens. This could be in a second pair of glasses or clip-ons.

Loss of contrast sensitivity, which is common to RK and PRK, can be simulated with diffusion filters. The diffusion filters also give somewhat of a halo effect that both surgical procedures may produce. Diffusion filters that rely on matrices inlaid into the lens may also give some star burst pattern the doctor or other interested party could demonstrate to a patient what a star burst may look like, by using a Cokin or Tiffin or other company's star burst filter. Star burst filters come in 4, 6, 8-spoke patterns. Four and 8-spokes would be most useful.

In all of the improved spectacle devices one does not have to worry about having only the central area of a lens with either a central haze or spokes, but the entire lens may be hazed or etched.

In each embodiment set forth above, the line of vision of the device, (e.g., contact lenses, eyeglasses, clip-on lenses or thin film press-on lenses), has been modified to produce the visual anomaly, and specifically, the field of vision on the lenses has been modified so as to simulate star-bursting or hazing, etc., which may result from PK or PRK.

In its broadest aspect this invention encompasses a modified lens designed to be worn in conjunction with eyeglasses and used for obtaining informed consent from a patient. The lens has a field of vision modified to simulate an ophthalmologic anomaly which may be the post-operative result of surgery. The modified lens when worn by a patient in conjunction with said eyeglasses will produce a visual anomaly and allow the patient to give the doctor competent informed consent. The modified lens can be contained in a loupe; or the lens can be contained in clip-on glasses, hinged clip-on glasses or slide-behind glasses.

The modified lenses as a pair can be designed to be worn in conjunction with eyeglasses. The lenses have their field of vision modified to simulate an ophthalmologic anomaly which may be the post-operative result of surgery. The modified pair of lenses can be contained in clip-on glasses, hinged flip-up glasses or slide behind glasses.

Eyeglasses with at least one modified lens are designed to be worn in conjunction with a second pair of eyeglasses, and will allow the patient to give the doctor competent informed consent. The eyeglasses may be slid behind glasses or eyeglasses having a clip or a hinged clip designed to be attached to a second pair of eyeglasses, and when worn with said second pair of eyeglasses will allow the patient to give the doctor competent informed consent.

This invention envisions modified thin transparent film press-on to be applied over the lens of eyeglasses and is useful in simulating an ophthalmologic anomaly which may be the post-operative result of surgery. The modified thin transparent film has markings such that its field of vision is modified to simulate said ophthalmologic anomaly, and when applied over the eyeglass lens of a patient will allow the patient to give the doctor competent informed consent.

The thin film can be made of plastic and is shaped to be able to fit onto the surface of an eyeglass. More specifically, the thin film is flexible plastic with a surface coated with adhesive to allow it to adhere to an eyeglass lens.

In ultimate use the lenses and eyeglasses of this invention are to be used for obtaining informed consent from a patient prior to ophthalmologic surgery. The method of use would comprise fitting over eyeglasses worn by said patient a lens or lenses whose field of vision has been modified to simulate a visual anomaly which may occur as a result of said surgery and then obtaining informed consent from said patient.

It is to be noted that the surface markings as well as contours could be made by stick-on transparencies onto the surface of the contact lens.

This invention contemplates lenses useful for simulating an ophthalmologic anomaly which may be the post-operative result of surgery. The lens or lenses have their fields of vision modified to simulate said ophthalmologic anomaly. The lenses have been modified to produce the glare and nocturnal starbursting experienced in radial keratotomy or the glare experienced after photorefractive keratectomy, e.g., the lenses may be hazed. Examples of the various embodiments involving hazing are hazed flip-up's, hazed slip behind glasses, hazed clip-on glasses, and by hazed peel-on's.

The technology for hazed lenses is commercially available. The technology is exemplified in a publication "The Photographers' Guide to Using Filters" published by Amphoto (1992). The hazing effect used for photography lenses could be applied to eyeglass lenses of this invention. Specific methods of hazing lenses can be created by mist-spray paint on the lens, emory or sandpapering the lens or heating plastic to produce the haze. The degree of hazing on the lens can vary from very light hazing to very intense hazing. In obtaining informed consent from the patient prior to surgery, the patient can try on and wear a series of eyeglasses with various degrees of a lens hazing. In this way, wearing eyeglasses with different degrees of hazing, the patient will be able to provide a more knowledgeable degree of informed consent to the doctor.

As a special embodiment of this invention, a contact lens or contact lenses have substantially their entire surface hazed. These hazed-surface contact lenses provide a convenient mode for a patient contemplating surgery to be able to access visual problems resulting from ophthalmic surgery and be able to give the doctor informed consent.

For obtaining informed consent from a patient prior to surgery, a modified lens or modified lenses placed in a card could be used. The card containing the lens or lenses therein could be held up to the eye for viewing and producing the visual anomaly which may result from contemplated surgery.

BRIEF DESCRIPTION OF THE DRAWINGS

FIG. 4 is a front elevational view of the contact lens with six radial lines.

FIG. 5 is a front elevational view of the contact lens with four radial lines.

FIG. 6 is a front elevational view of the contact lens with slight hazing.

FIG. 7 is a front elevational view of the contact lens with moderate hazing.

FIG. 8 is a front elevational view of the contact lens with substantial hazing.

Figure 1:
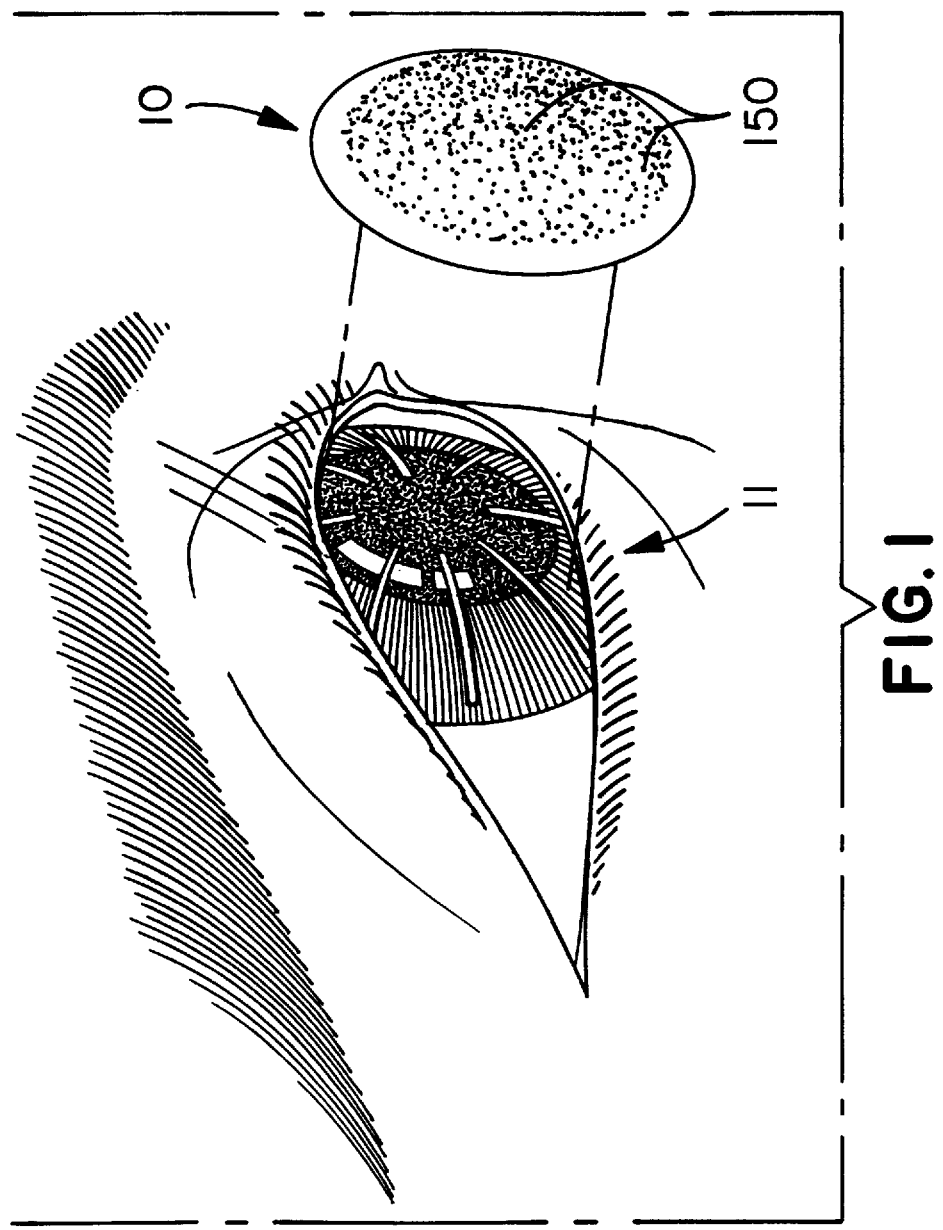
FIG. 1 is perspective view of the contact lens of this invention about to be fitted into the eye. The contact lens having eight radial lines.

In many of the eyeglasses set forth in the drawings, the temple of the eyeglasses has been omitted for ease of illustration.

DESCRIPTION OF THE PREFERRED EMBODIMENTS

With reference to FIG. 1, a contact lens 10 of this invention about to be fitted into the eye 11 has eight radial lines 12. The contact lens 10 with radial lines 12 when worn will simulate glare and nocturnal starbursting, a visual anomaly which may result from radial keratotomy (RK).

Figure 2:
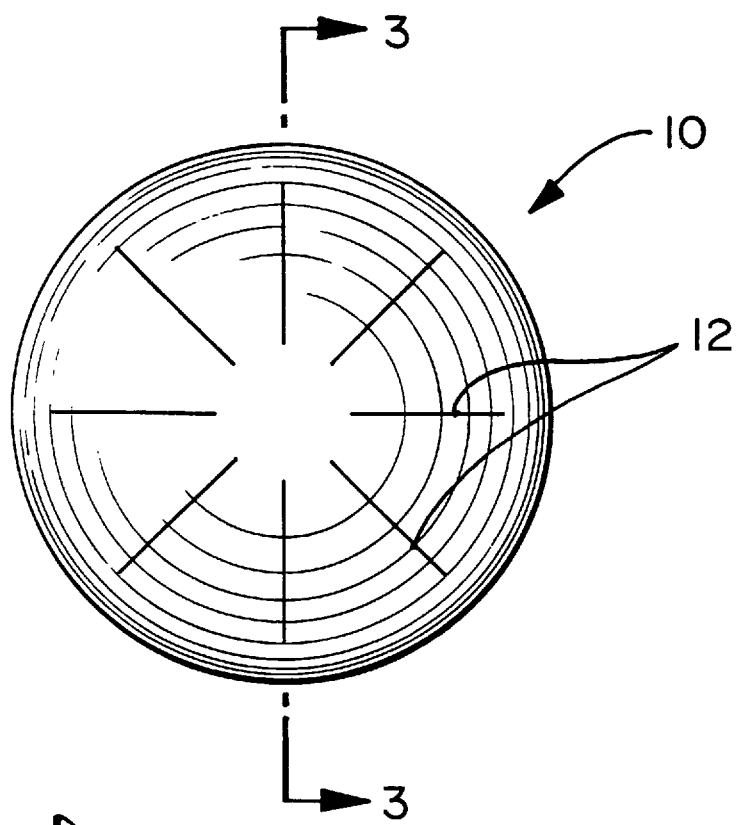
FIG. 2 is a front elevational view thereof.
Figure 3:
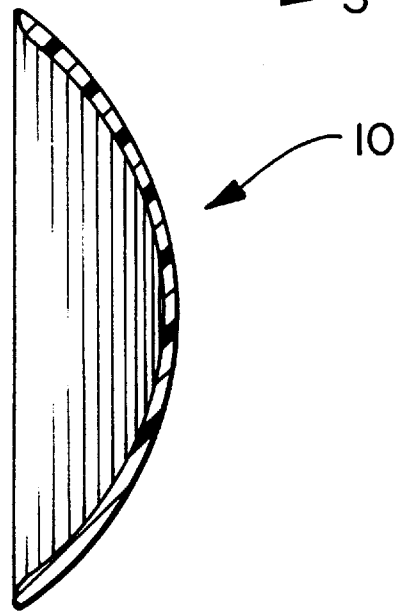
FIG. 3 is a cross-sectional view taken along lines 3—3 of FIG. 2.

The contact lens 10 can be a conventional contact lens 10 (FIGS. 2 and 3) which has had its field of vision modified by etching, dying, etc. to form the lines 12 or other contemplated configurations (FIG. 2).

The contact lens 10 to simulate glare and nocturnal starbursting may have a varying number of radial lines 12. FIGS. 2, 4 and 5 are examples of lenses 10 with radial lines 12 producing varying degrees of glare and nocturnal starbursting.

In the case of RK, the visual effects of the lenses 10 are created by making radial lines 12 on or in the lenses 10 in the same patterns that are incised into the cornea in performing RK. Four, six or eight radial lines 12 would be made with optical zones of 1.75 to 5.0 mm (RK optical zone range) extending toward the rim of the lens to a diameter of from 10 to 12 mm. The lines 12 would be 0.1 to 1.0 mm wide and white in color. The lines would most ideally be laser etched onto the soft contact lens (SCL) or the lines could be fine ridges or depressions molded into the lens when manufactured. Opacity could be created by molding fine cross hatching, dimples or parallel lines in the same dimensions used by lens manufacturers when imprinting SCLs with parameter and brand logo indicators. Height or depth of molded lines are in the tenths of mm. Hatching, etc. would be in the hundredth to tenths of mm (ex. illustration of B&L disposable lens). Alternatively, various lines and patterns can be painted on the surface of the lens (like in opaque colored cosmetic contacts) or dyed onto the lens or created with a photo engraving process. Ideally, the lines 12 should extend through the substance (e.g., plastic) of the CL to give some of the depth such as actual RK scars exhibit. Actual scars are 100% of the corneal thickness as measured in the para central zone by ultrasound contact pachymetry (0.500 mm±0.100 mm).

The glare which may be experienced after photorefractive keratectomy (PRK) may be simulated by a slight hazing 13 of the central 3 to 6 mm of the contact lens 1 (FIG. 6).

In the case of PRK, the central cornea is ablated with an excimer laser in an optical zone of 6.0 mm±2 mm to achieve a central flattening to correct myopia. As the cornea heals, this area may develop a fine reticular haze that may take several months to fade and may be permanent. This haze gives a glare, slight blur or a loss of contrast sensitivity. The effect of the haze is most prominent at night when bright oncoming lights may give a glary "dirty windshield" effect. To simulate the optical aberrations of PRK the 6.0±2 mm optical zone of the SCL would be modified to create a fine hazy pattern similar to that of a healing cornea. Actual photographic examples of clinical haze may be used as models to determine the degree of opacity. The front surface of the contact lens may be modified to create the anterior irregular astigmatism that develops as the cornea epithelium heals and the regeneration of new stromal collagen occurs. Central corneal islands (irregular areas of ablation) may be simulated by the contact lens, as well. If there are measurements or units of light scatter used in physical optics, the required amount or degree would be mild in the case of PRK modeling (as compared to say cataracts where significant scatter/opacity would be indicated). Techniques similar to those used for the RK SCL could be employed e.g., molding, laser etching, dying, painting or photographic processes.

Macular degeneration and cataracts may be simulated by darker or more intense central (optical zone) hazing 14 of the contact lens 10 (FIGS. 7–8).

Figure 9:
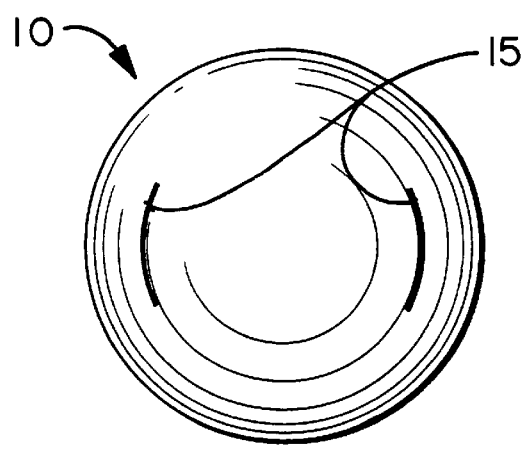
FIG. 9 is a front elevational view of the contact lens with paired arcuate cuts.
Figure 10:
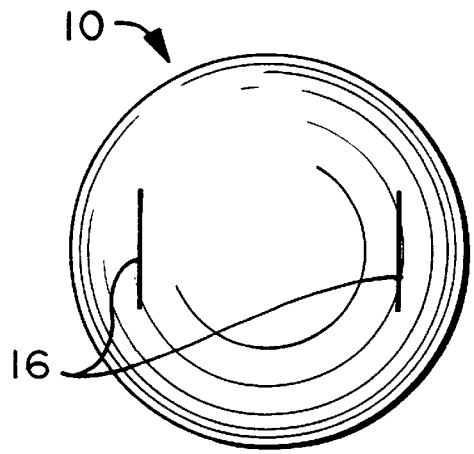
FIG. 10 is a front elevational view of the contact lens with paired "T-cuts".

With reference to FIG. 9 a lens 10 with paired arcuate cuts 15 approximately 6 mm apart; and with reference to FIG. 10 paired "T-cuts" 16 approximately 6 mm apart. The lenses of FIGS. 9 and 10 are of a size to cover the cornea. Arcuate 15 or T-cuts 16 for AK could be simulated (astigmatic cuts), although these cuts would probably be less useful since they would be as pairs 180 degrees apart, at a 6 mm optical zone (and 30 to 90 degree extent), and may be far enough away from the optical zone that they would not create much visual effect.

Other medial opacities, such as corneal scars, corneal edema or cataract, could be simulated by creating central optical zone haze 14 or opacity of denser magnitude to decrease light transmission and increase light scatter. [Scatter effects would be more important than reducing light transmission; as sun glasses that have only 50% or 10% transmission may allow persons with normal vision to still see satisfactorily.] Sufficient haze to reduce vision to say 20/50 or 20/60 would demonstrate moderate clinically significant disease and reductions to 20/200 or 20/400 would demonstrate advanced opacities. Wedge-shaped clefts, variable opacity and brown discoloration in the lenses would produce an effect similar to actual cataracts.

Figure 11:
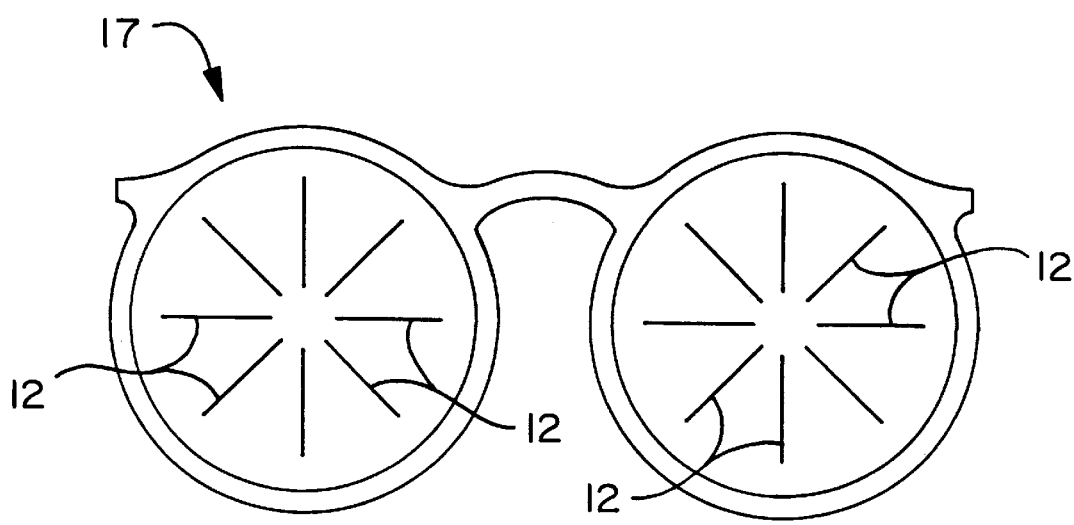
FIG. 11 is an elevational view of eyeglasses with lenses marked with radial lines.
Figure 12:
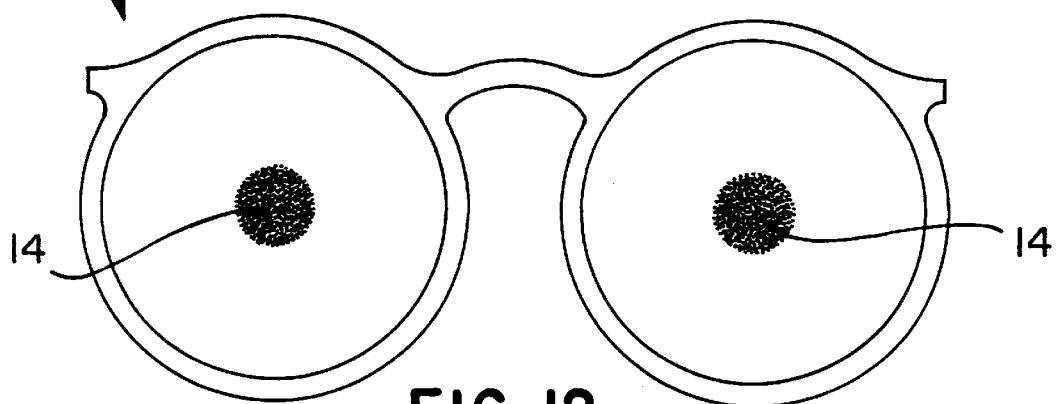
FIG. 12 is an elevational view of eyeglasses with central hazing.

There are times when the patient will not be able to wear contact lenses. With this being the case this invention supplies eyeglasses 17 with various markings simulating visual anomalies (FIGS. 11–12). FIG. 11 simulates starbursting and the hazing 12, and FIG. 12 simulates glare 14 which may be experienced after RK and PRK, respectively.

Figure 13:
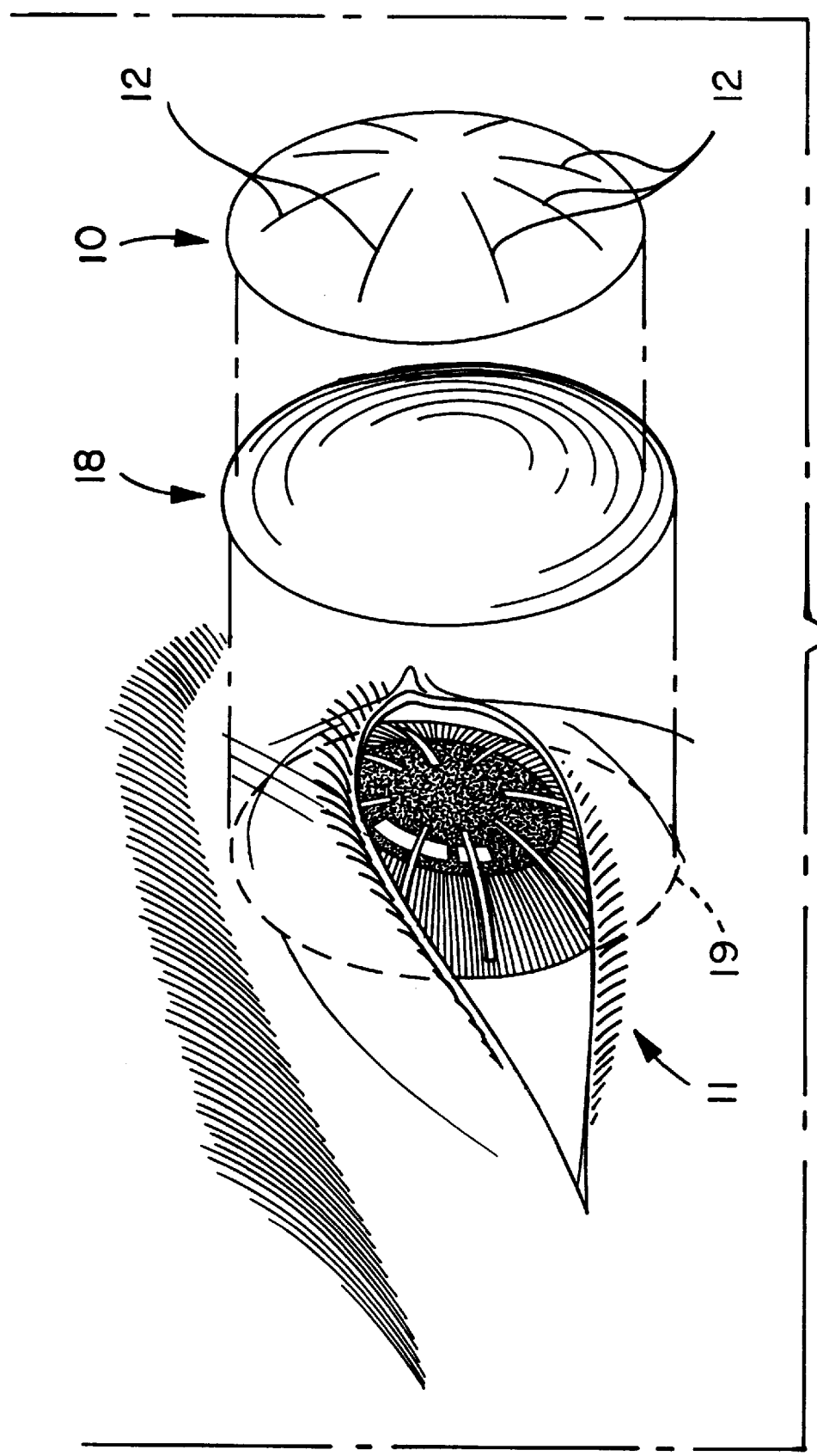
FIGS. 13 and 14 are views illustrating contact lenses of this invention worn piggyback, one lens over the other.
Figure 14:
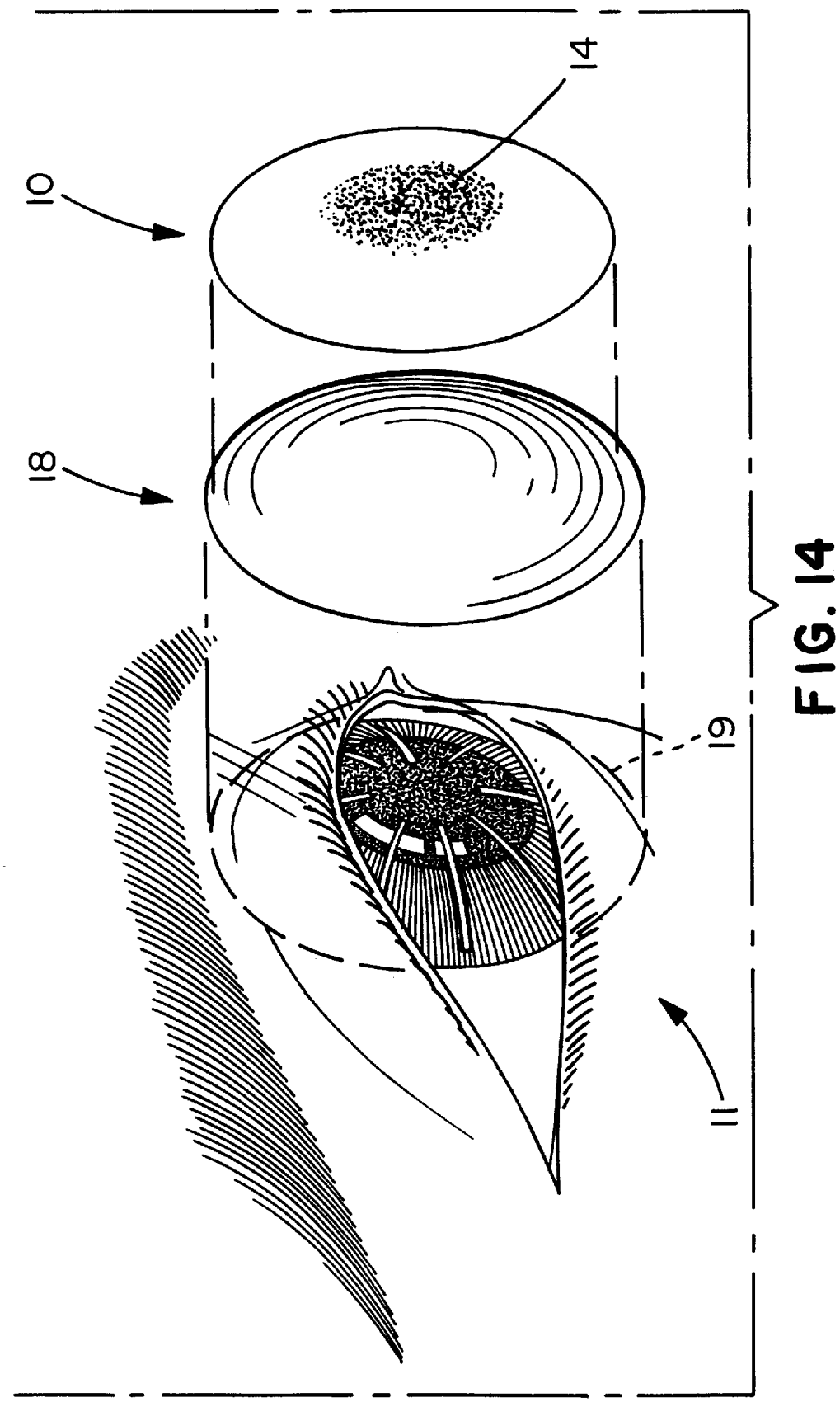

The contact lenses of the invention would be worn piggyback (FIGS. 13 and 14). That is the en. contact lens with the altered field of vision could be worn over the patient's prescription contact lens (FIGS. 13 and 14).

Figure 15:
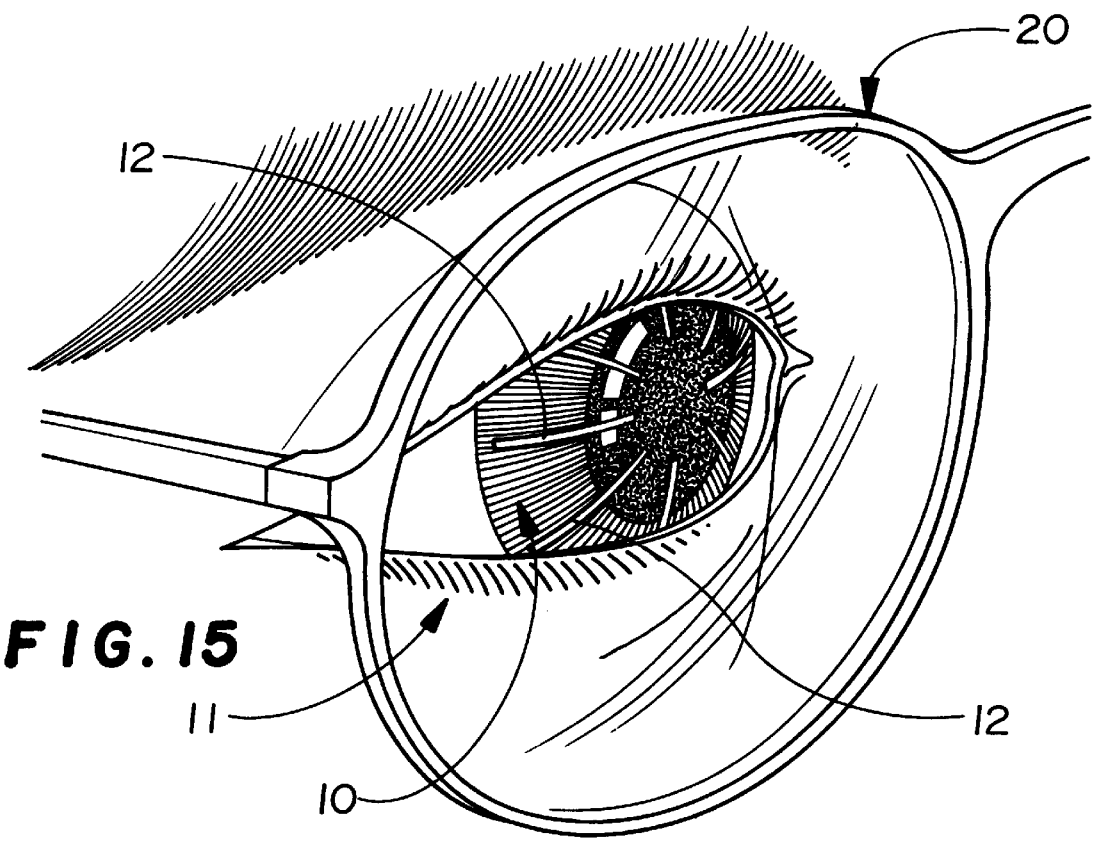
FIG. 15 is a view illustrating contact lenses of this invention worn under eyeglasses. The eyeglasses are only partially shown for ease of illustration.

With reference to FIG. 13 the contact lens of this invention 10 with radial lines 12 is worn over the patient's prescription contact lens 18, and in FIG. 14 the contact lens 10 with hazing 14 is worn over the patient's prescription contact lens 18. The dashed lines 19 in FIGS. 13 and 14 represent the area of placement of the contact lenses 10 and 18 in the eye 11. The contact lens 10 besides being worn in conjunction with prescription contact lenses 18, can be worn along with a patient's prescription eyeglasses 20 (FIG. 15). With the contact lens 10 worn piggyback over the patient's prescription CL 18, or in conjunction with prescription eyeglasses 20, the patient will be able to attain a more accurate assessment of possible visual aberrations prior to surgery and thereby give more meaningful informed consent.

Additional embodiments of this invention are possible as further exemplified.

The size of the optical zone can cause visual problems. A small optical zone may create halos, especially at night when the pupil may dilate to be larger than the optical zone. This problem is frequently seen with excimer PRK when used to correct higher degrees of myopia. This type of distortion may be simulated by limiting the optical zone of the contact lens to the maximum possible with PRK (approximately 6 mm with current technology). The 6 mm optical zone may be a blend with only the center of the zone (3 or 4 mm) possessing the full optical power required.

The accuracy of RK and PRK optical correction is limited. Some patients will have uncorrected vision of 20/20; however, some will have vision of 20/40. (Based on most studies for corrections of up to −6.00 diopters.) This is in part due to over and under corrections. Under corrections may be simulated by having a degree of residual myopia, perhaps −0.50 to −0.75 diopters from the ideal correction; e.g. too weak a contact lens correction. Conversely, over corrections can be simulated by too strong a contact lens. These over and under corrections may be achieved by selecting a CL with slightly greater or lesser power than ideal or by having a small degree of plus or minus correction in a piggyback CL. An over correction of a myope would correct too much myopic or minus power, adding too much plus or hyperopic power, thus leaving the patient net plus.

Astigmatic correction deficiencies may be simulated with lenses that do not fully correct the astigmatism.

Each of the types of CL simulation may be used singly or in combination, either in a single CL or in a set of CL's.

A noteworthy embodiment of this invention envisions a set of modified contact lenses of this invention supplied in a kit. Lenses with radial lines, hazing, etc. would be included in the kit. The kit with the lenses would be convenient for supplying the doctor with contact lenses and could be supplied and used as an educational tool in the classroom. The kit and/or lenses may be disposable.

It is obvious to those skilled in the art that lenses with modified fields of vision simulating visual anomalies could be incorporated into a phoropter or trial lens set. The doctor could use such a device for obtaining informed consent from a patient.

Figure 16:
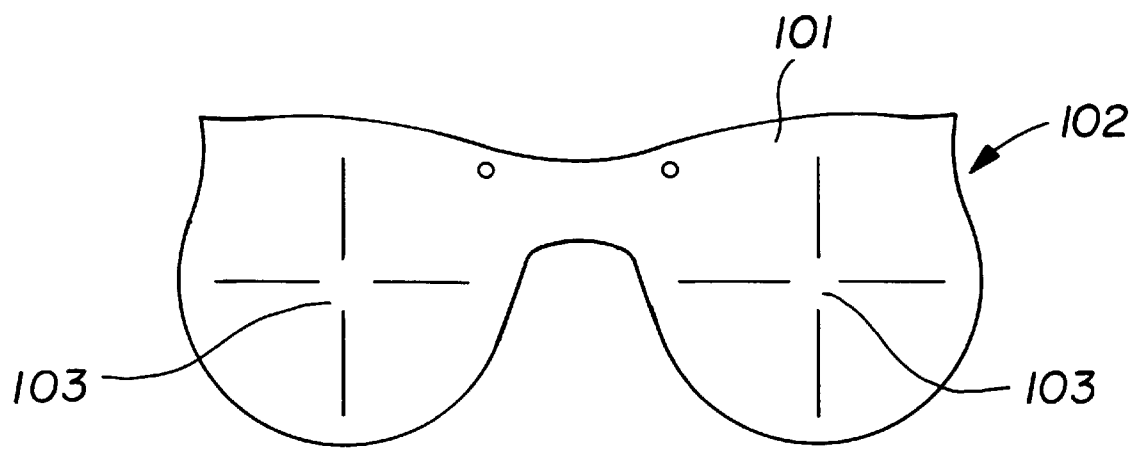
FIG. 16 shows a front view of clip-on glasses.
Figure 17:
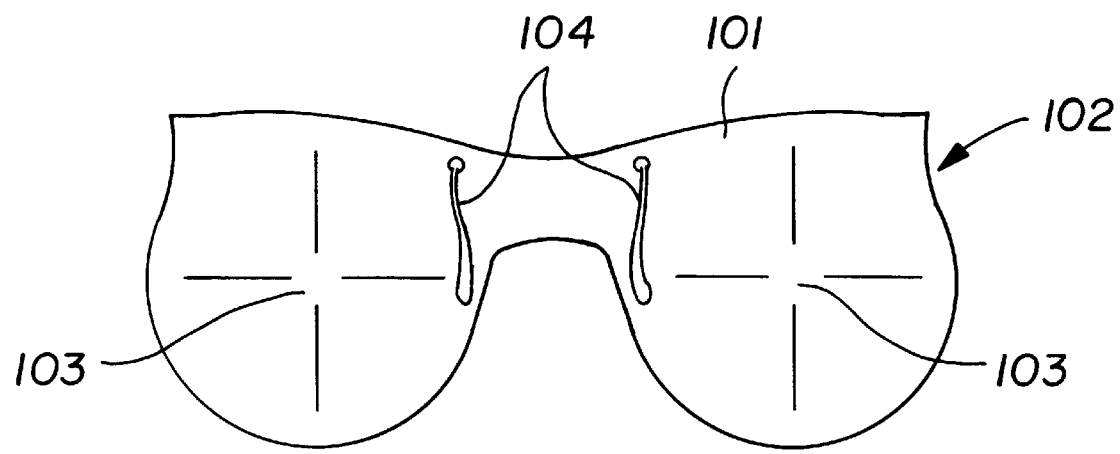
FIG. 17 is a rear view thereof.

With reference to FIGS. 16 and 17, there is illustrated the front view 100 and rear view 101, respectively, of clip-on glasses 102 with the line of sight modified to simulate starburst 103. The clips 104 are used to clip the clip-on glasses 102 to eyeglasses (not shown).

Figure 18:
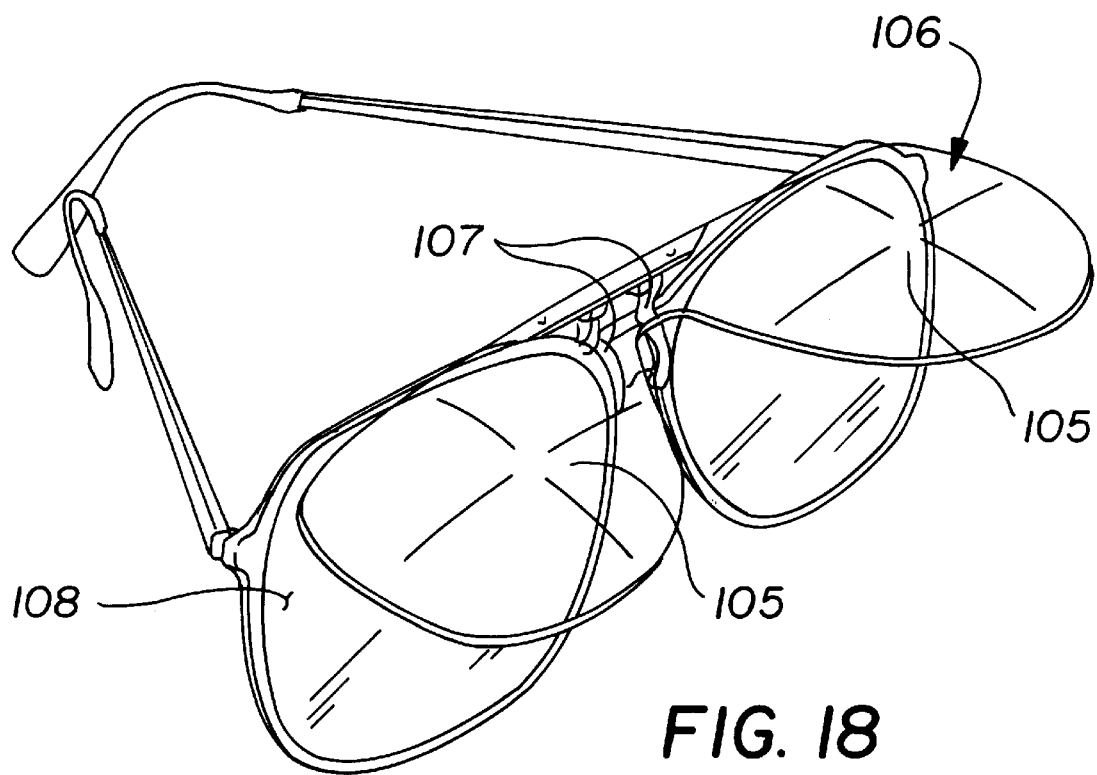
FIG. 18 is a view illustrating a hinged visor on glasses.

Referring now to FIG. 18 the modified lenses 105 can be a visor 106 hinged at 107 and attached to regular eyeglasses 108.

Figure 19:
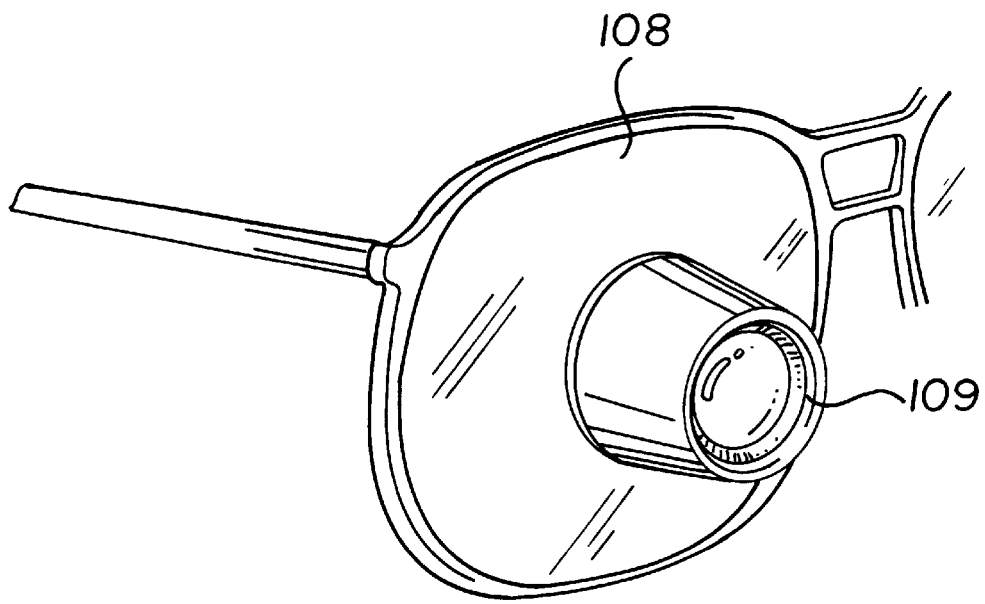
FIG. 19 is a view illustrating loupes to be fitted over eyeglasses.

The modified lenses can be fashioned into loupes 109 to be used in conjunction with eyeglasses 108 or spectacles 108 (only partially shown) (FIG. 19).

Figure 20:
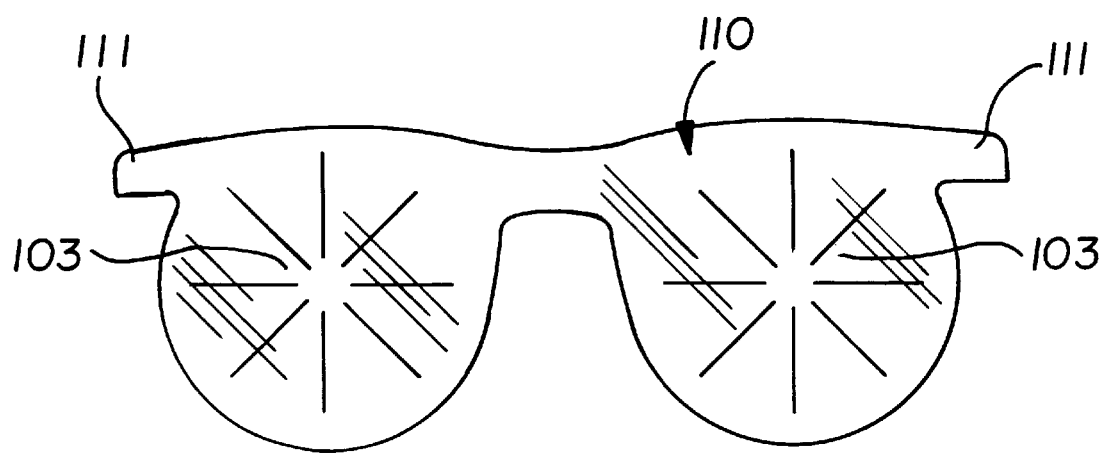
FIGS. 20–21 are front views of glasses for sliding behind a pair of worn eyeglasses.
Figure 21:
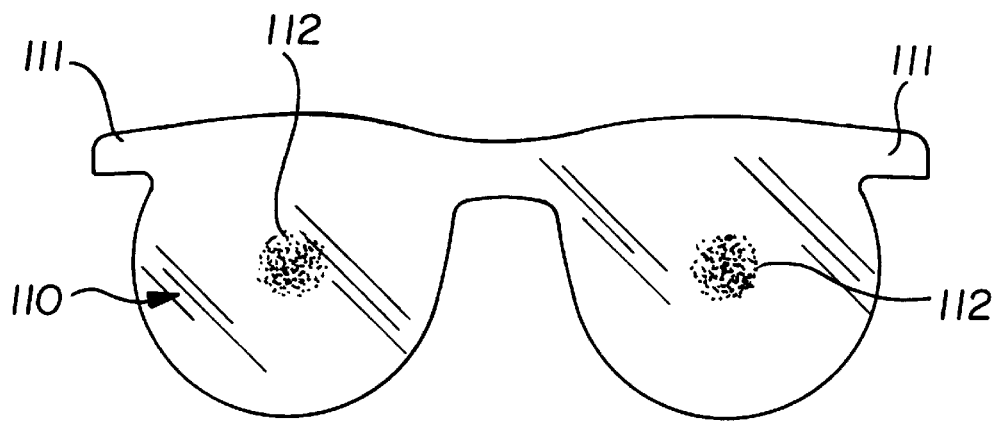

Slide behind lenses 110 with tabs 111 (FIGS. 20 and 21) can be worn in conjunction with eyeglasses (not shown). The line of sight has been modified to simulate starburst 103 or glare 112. These slide behind lenses 100 are generally made of plastic and are designed to slide behind the lenses of eyeglasses regularly worn by a patient.

Figure 22:
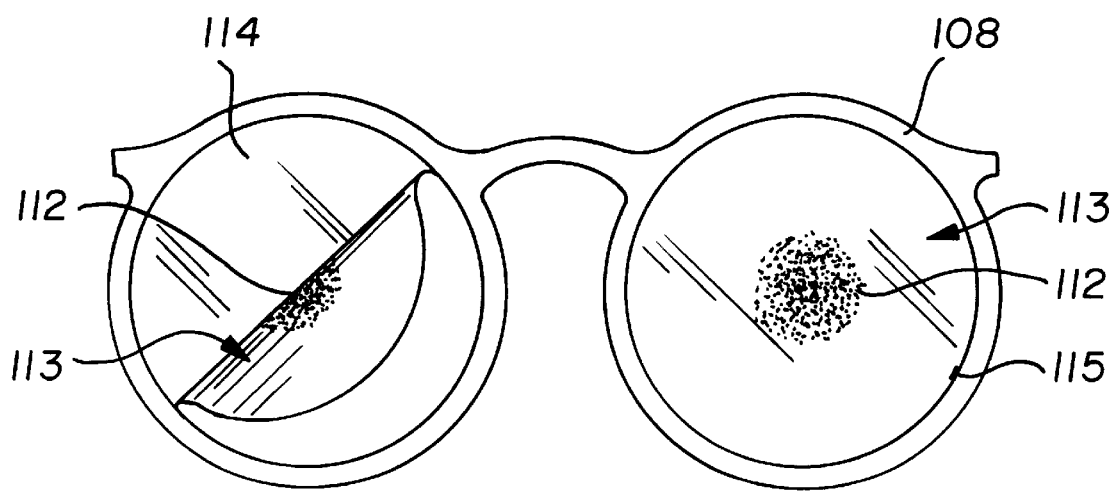
FIG. 22 is a view illustrating a modified thin transparent film press-on for application to eyeglasses.

A modified thin transparent film press-on 113 can be applied to the patient's own eyeglass 108, to produce visual distortion, e.g., glare 112 (FIG. 22). In FIG. 22 the modified thin transparent film press-on 113 is being applied to the lens on the left 114 and is already in place as applied to the lens on the right 115.

An enhancement of the spectacles for simulating glare and loss of contrast sensitivity from laser vision correction. The diffusion filter lens can have a graduated or multiple degree of simulate severity in an individual lens.

Figure 23:
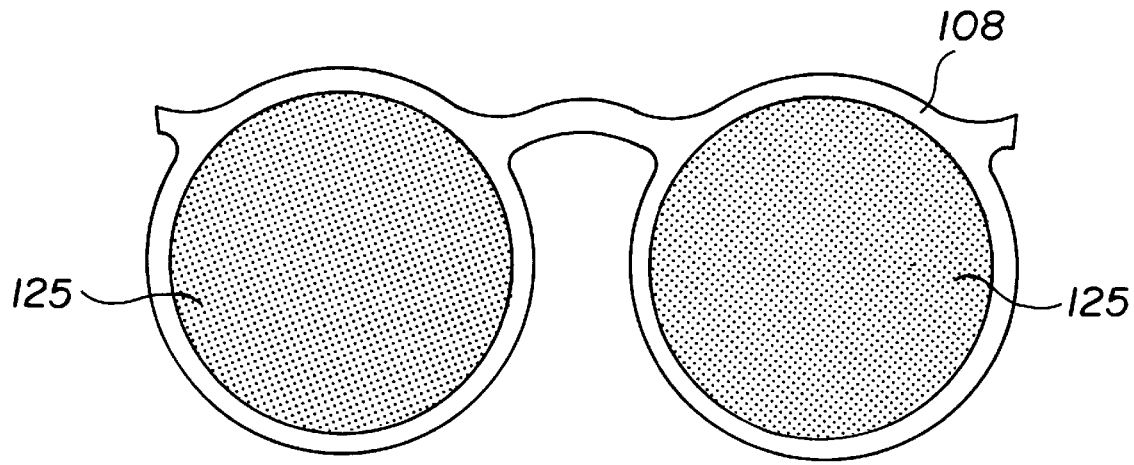
FIG. 23 is a view of eye glasses with the entire lens hazed.

A special embodiment of this invention envisions an eyeglass with hazing 125 over the entire lens (FIG. 23). The purpose of the hazing 125 is to mimic the visual hazing which could result from refractive surgery.

Figure 24:
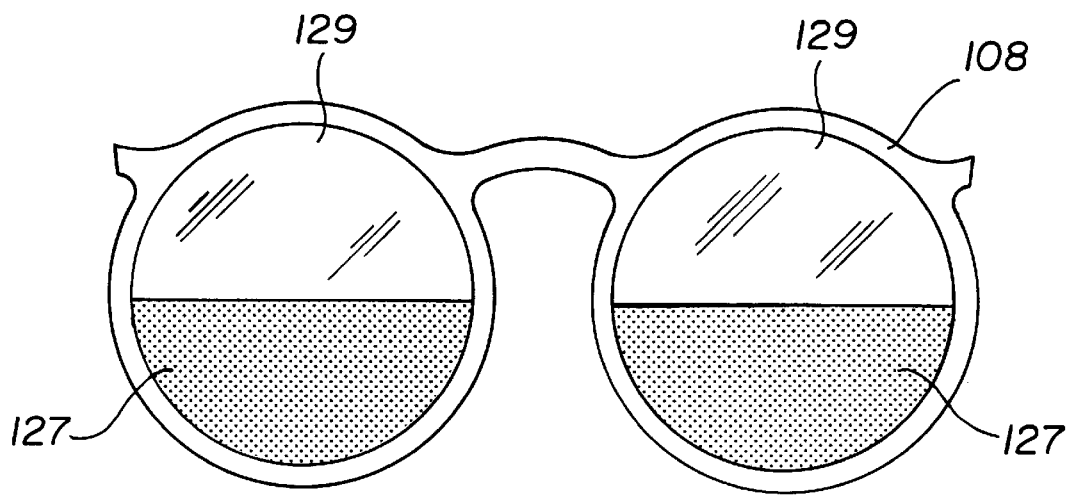
FIG. 24 is a front view of bifocal eyeglass with the top portion plain and the bottom portion hazed.

Referring to FIG. 24, for better experiencing the contrast between hazing and no hazing eyeglasses 108 are provided with partial hazing 127 at the bottom of the lens and a clear portion 129 at the top of the lens.

Figure 25:
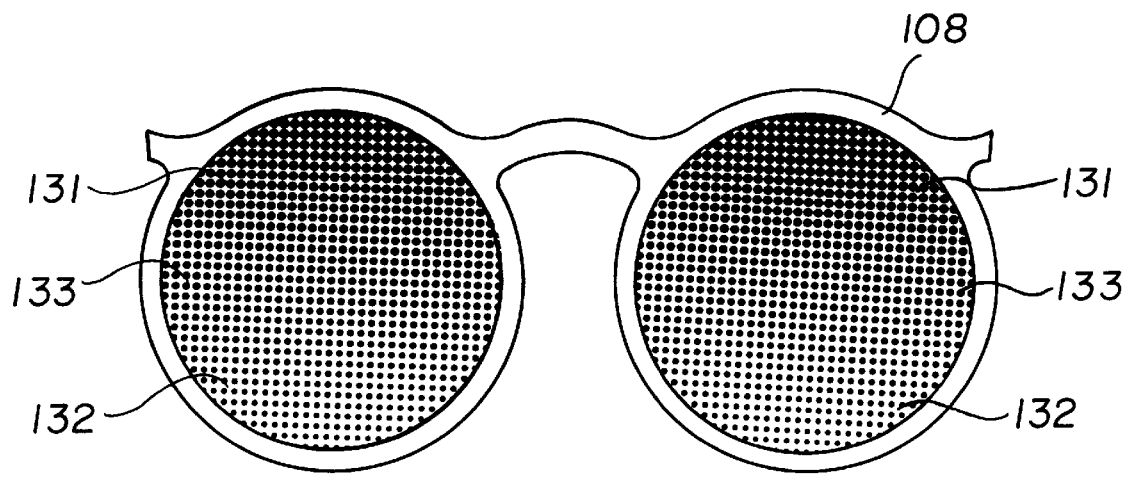
FIG. 25 is a front view illustrating eyeglass lenses having bifocal fields of hazing. The top of each lens being more intensely hazed than the bottom. The top and bottom fields are merged or blended into each other.
Figure 26:
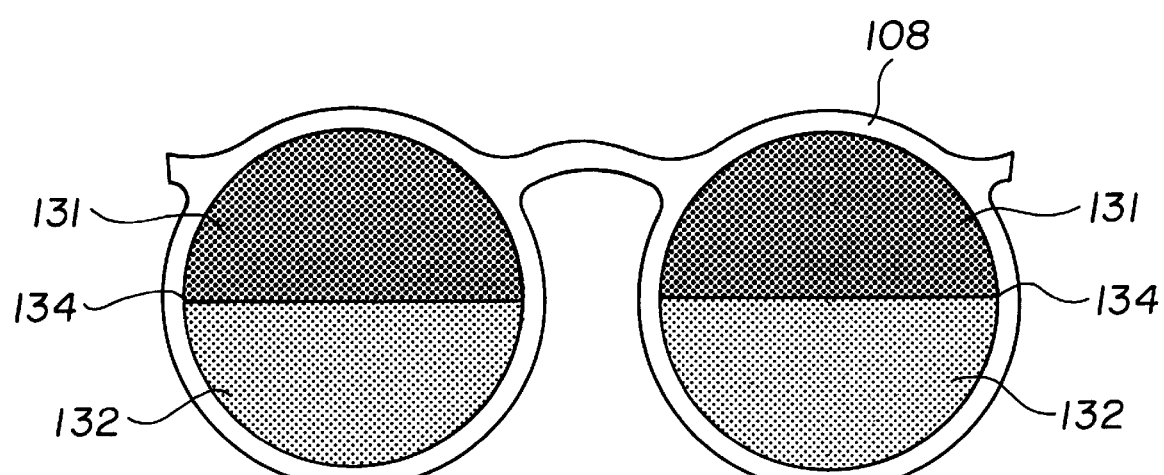
FIG. 26 is a front view illustrating eyeglass lenses having bifocal fields of hazing. The top of each lens being more intensely hazed than the bottom. The fields are set off by a line of demarcation.

Referring to FIGS. 25 and 26, eyeglasses 108 have surface modifications to depict various degrees of hazing. FIGS. 25 and 26 illustrate severe hazing 131 at the top of the lens, and milder hazing 132 at the bottom of the lens. In FIG. 25 the gradations of hazing, one to the other, are blended or merged 133, while in FIG. 26 the gradations, one to the other, are distinctly marked by a line of demarcation 134.

Figure 27:
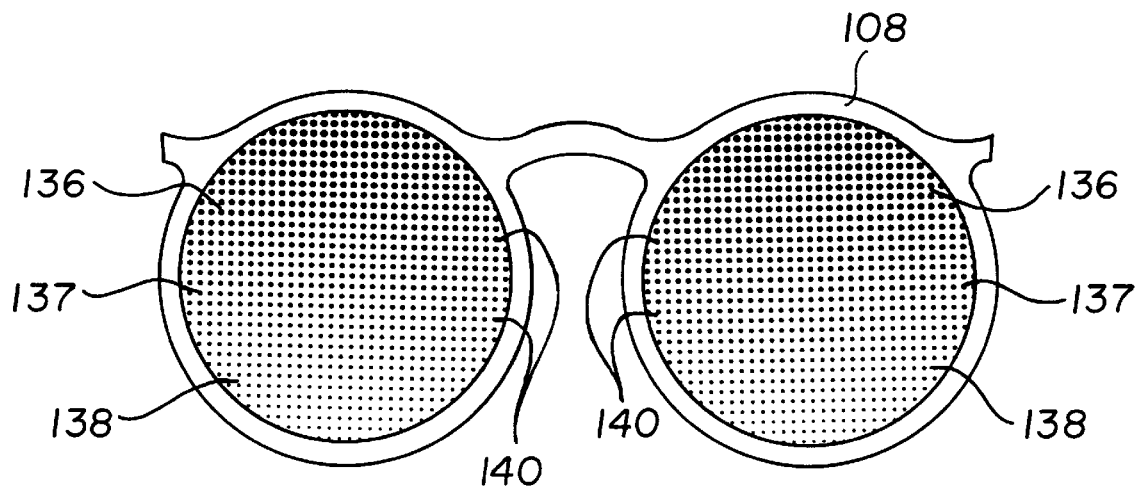
FIG. 27 is a front view illustrating eyeglass lenses with trifocal fields of hazing. The fields of hazing are merged with the top field being more intensely hazed than the bottom.
Figure 28:
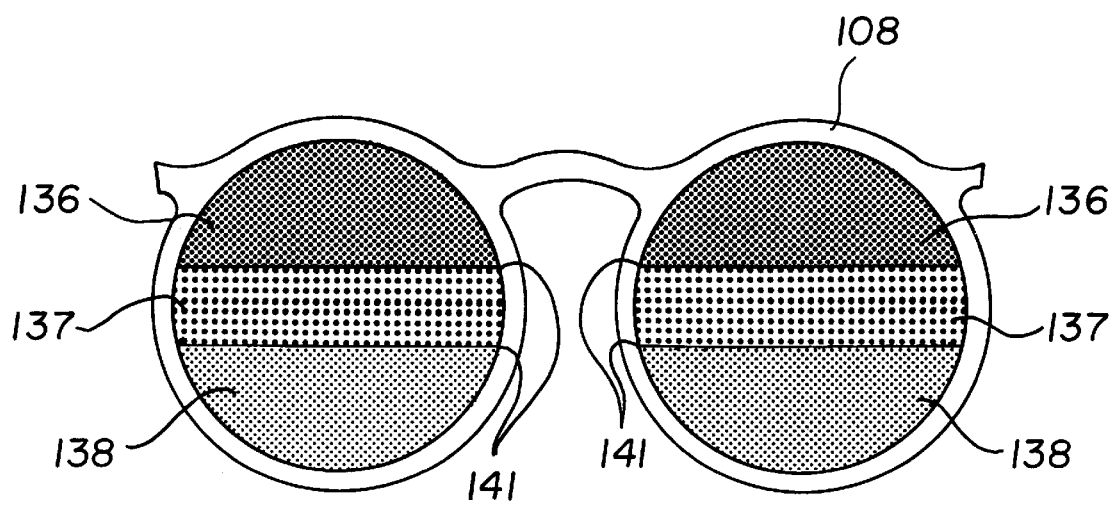
FIG. 28 is a front view illustrating eyeglass lenses with trifocal fields of hazing. The fields are set-off by a line of demarcation.

Referring to FIGS. 27 and 28 eyeglass lenses of different diopters are shown. The upper part of the lens could be minus, e.g., −1 diopter 136, the center portion 137 could be plano and the bottom portion 138 could be plus e.g., +1 diopter. The three fields could be made distinct (FIG. 27) or gradually merged (FIG. 28). Of course, instead of trifocal lenses, the lens could be bifocal. Progressive embodiments of this concept can be achieved by using a progressive lens of −1.00 diopter with a plus +200 ADD. One would desire a lens with a broad width to the ADD and a larger intermediate zone. The magnitude of lens and ADD may vary from ±0.25 diopter ± diopters may vary from ±0.25 diopters to ±3 diopters.

Figure 29A:
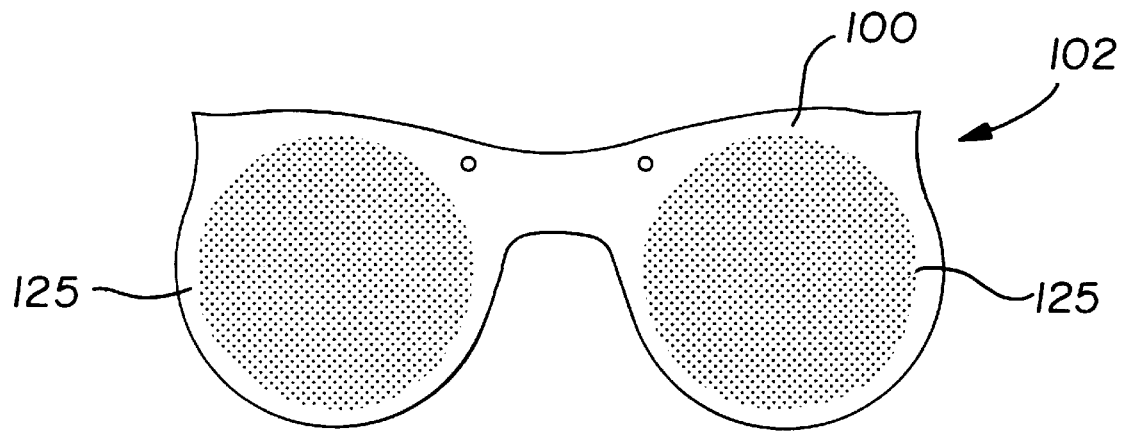
FIG. 29A is a front view of clip-on glasses with bifocal hazing.
Figure 29B:
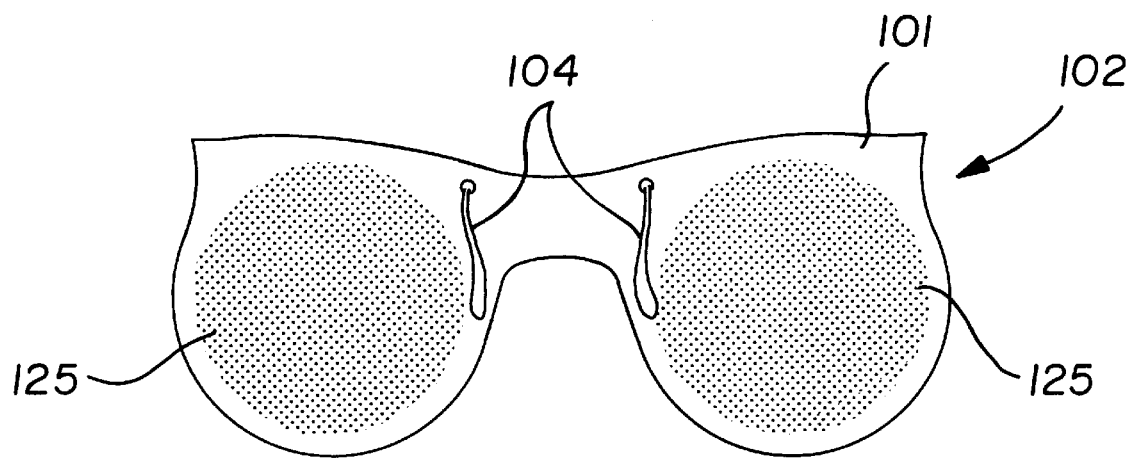
FIG. 29B is a rear view thereof.

With reference to FIG. 29A and 29B clip-on glasses 102 have hazing 125. FIG. 29A is a front view 100 and FIG. 29B is a rear view 111. The lens can be hazed 125 either front or back.

Figure 30:
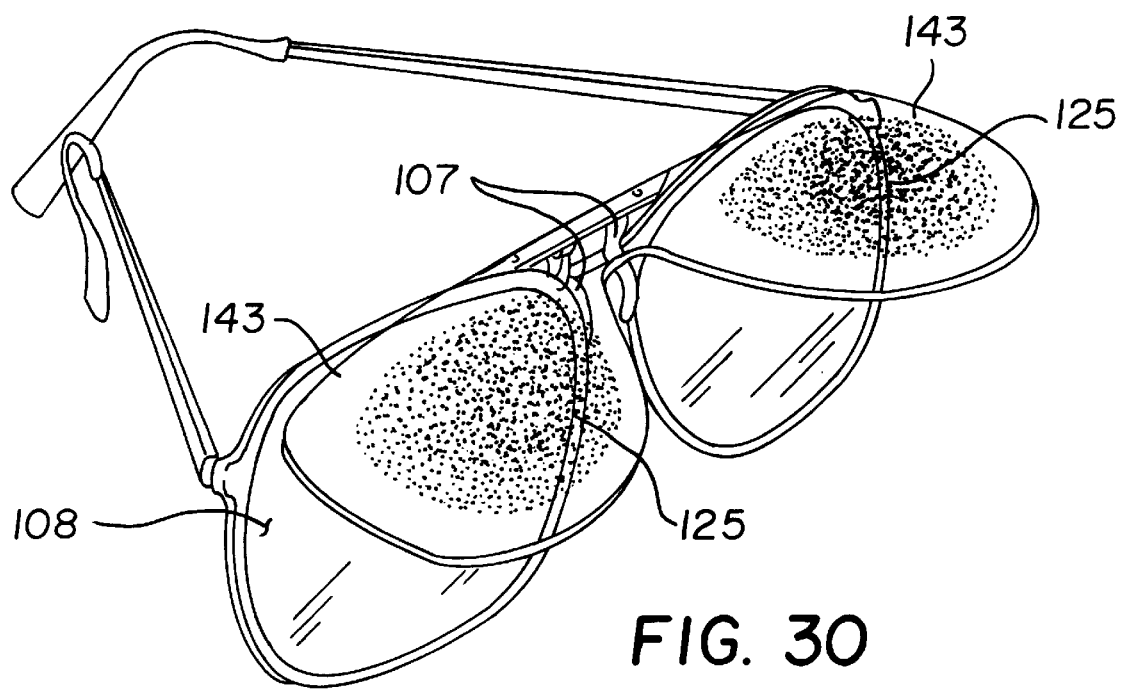
FIG. 30 is a view illustrating eyeglasses with hazed flip-up lenses.
Figure 31:
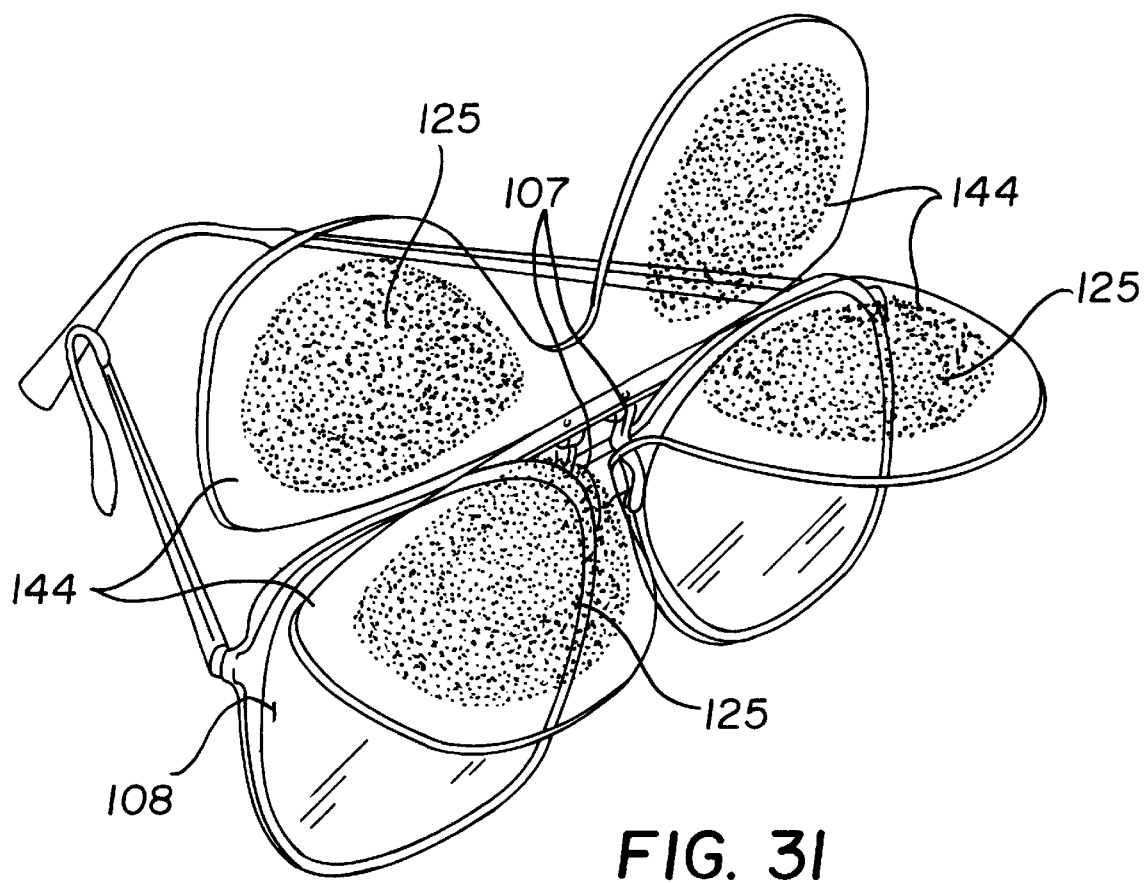
FIG. 31 is a view illustrating eyeglasses with double flip-up lenses.

Referring to FIG. 30 an embodiment of this invention in which a flip-up lens 143 attached to eyeglasses 108 are hazed 125. Contemplated by this invention are eyeglasses 108 having attached thereto multiple flip-up lenses 144 having hazing 125 applied thereto (FIG. 31). By flipping down one or more lenses hazing may be varied by degrees. With two lenses flipped down hazing will be most severe. With only one lens flipped down, hazing will be least severe.

Figure 32:
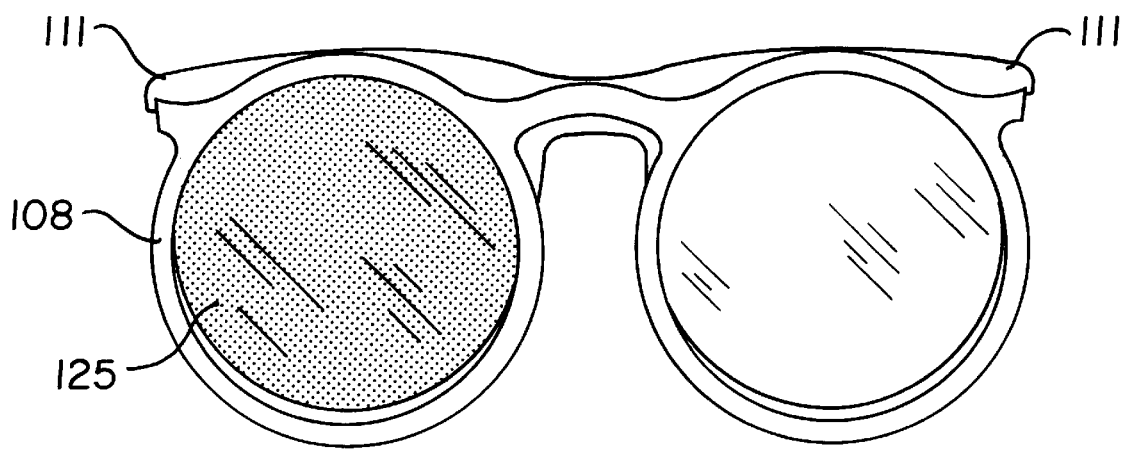
FIG. 32 is a view illustrating a hazed slip-behind lens with a single lens hazed.

FIG. 32 describes slip behind lenses 111 with hazing 125 that are being used with eyeglasses 108. Only one lens is shown hazed.

Figure 33:
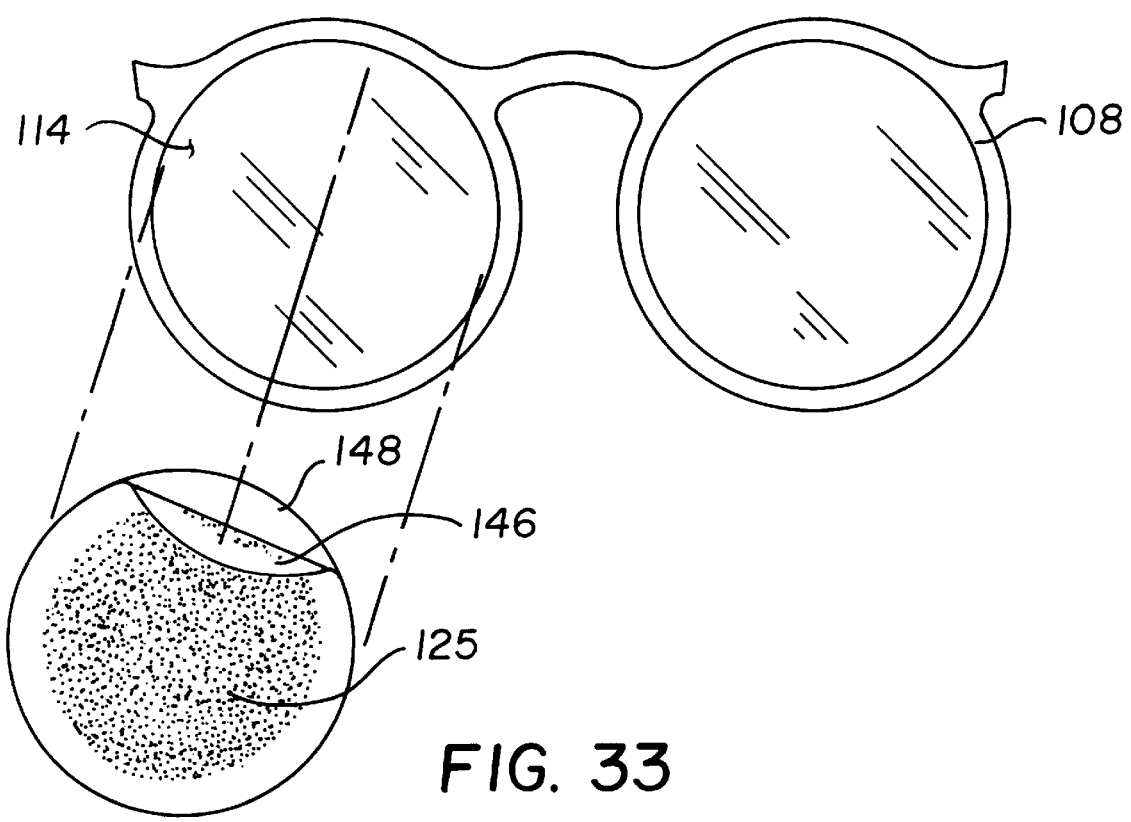
FIG. 33 is a view illustrating a peel-on for hazing an eyeglass lens.
Figure 34:
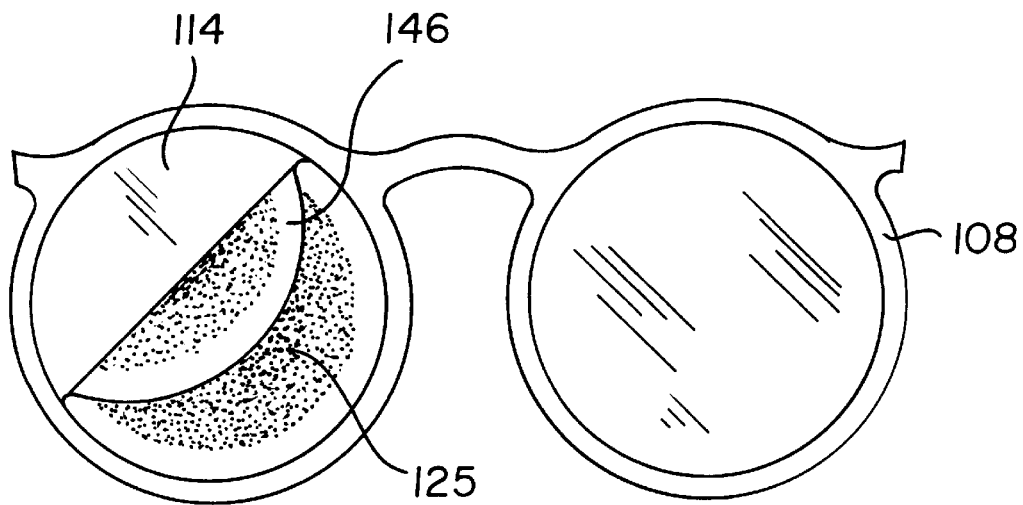
FIG. 34 is a view illustrating a hazed peel-on being applied to a lens.
Figure 35:
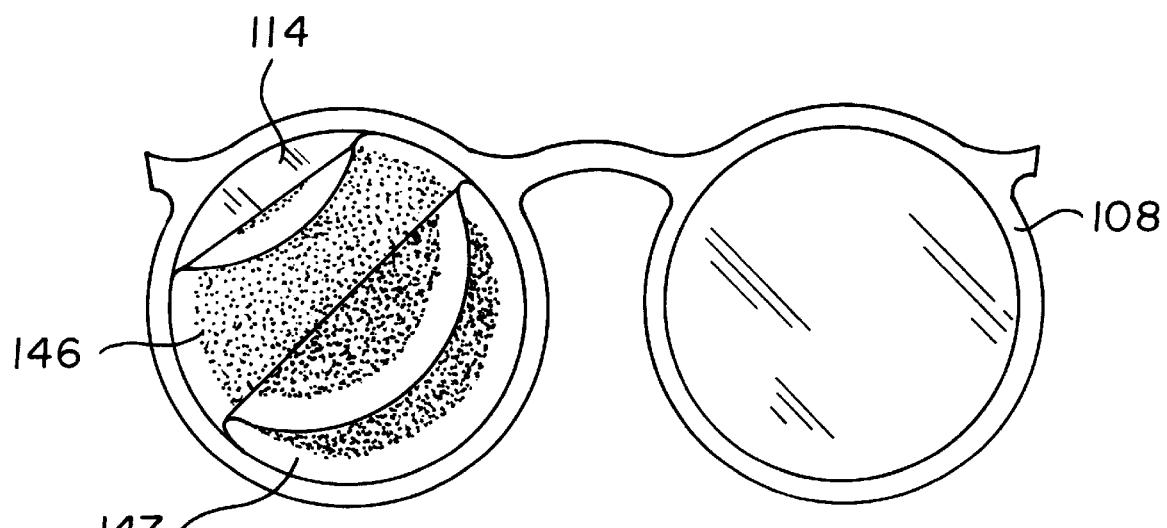
FIG. 35 is a view illustrating a second hazed peel-on being applied over a peel-on already applied to the lens.

Referring to FIGS. 33–35 a unique embodiment of this invention contemplates a plastic peel-on 146 to produce the hazing 125 on the lens 114 of a patient's eyeglasses 108. FIGS. 33 and 34 describe a single peel-on 146 to produce minimum hazing. With reference to FIG. 35, a more intense hazing can be produced by adding an additional hazed peel-on 147 to the hazed peel-on 146 already in place on the lens of eyeglass 108. For convenience the peel-on 146 (or 147) is supplied mounted on a backing 148 which protects the adhesive on the peel-on.

It is evident from a simple viewing of the figures set forth in the drawings that the entire field of vision can be hazed. For example, the field of vision of a single lens, as well as the fields of vision of bifocals, trifocals, etc.

Figure 36:
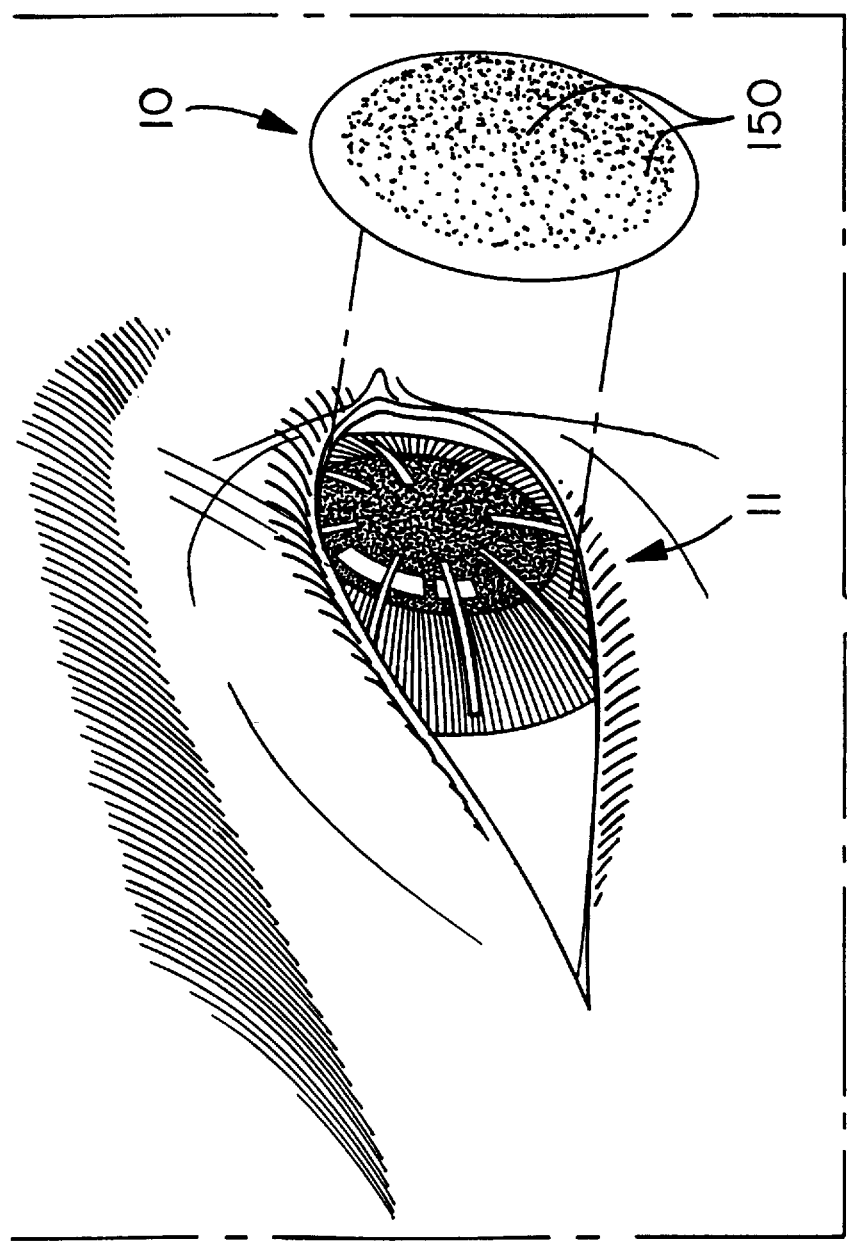
FIG. 36 is a view illustrating a contact lens with the entire field of vision hazed. The lens is being applied to the eye.

In addition, contact lenses (FIG. 36), as well as eyeglass lenses, can be of the patient's prescription and can have substantially the entire lens hazed. In FIG. 36 the contact lens 10 with hazed surface 150 is about to be placed in the eye 11.

Figure 37:
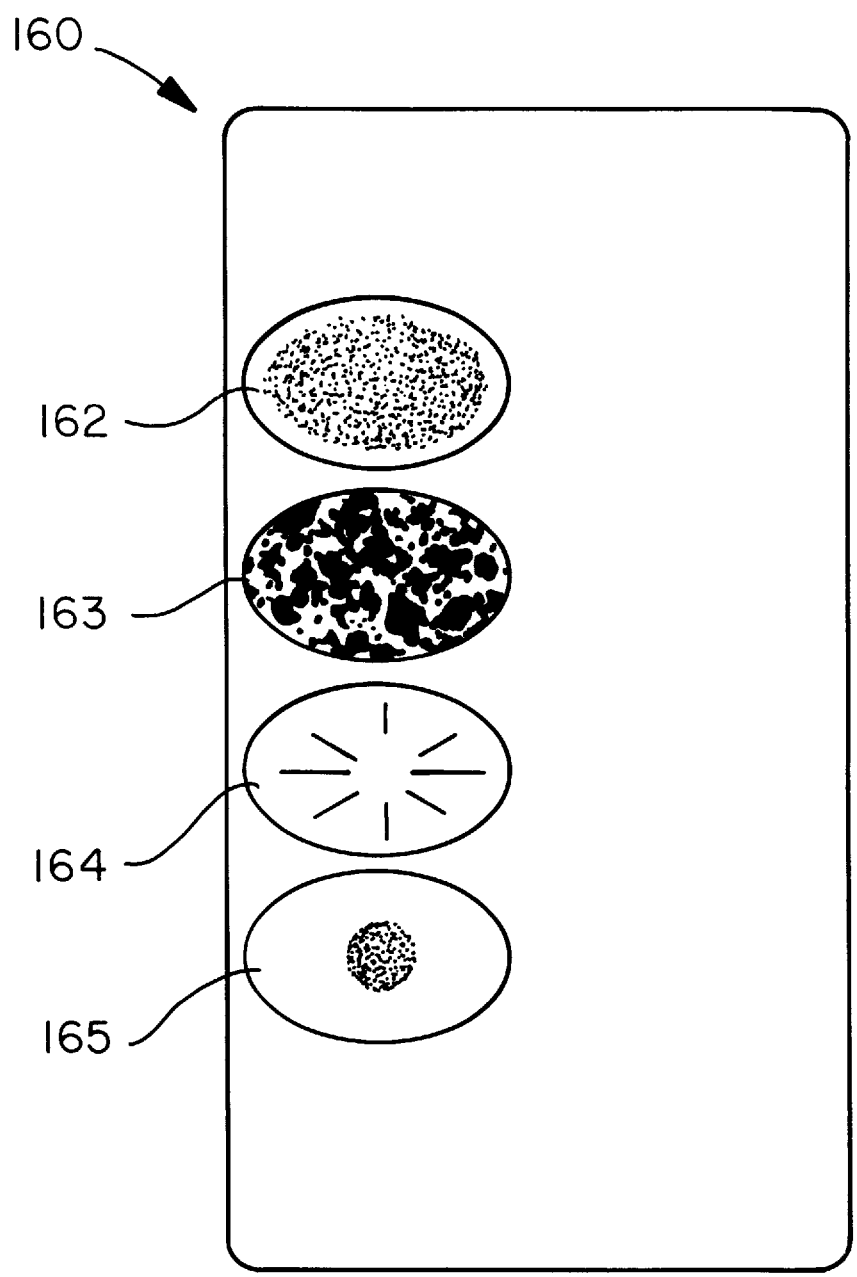
FIG. 37 is a view illustrating a card containing modified lenses.

Referring to FIG. 37, a card 160 having placed therein a series of lenses 162–165 can be held up to the eye to mimic visual anomalies which may result from ophthalmic surgery. The card 160 has a hazed lens 162; a mottled lens 163; a lens mimicking star-burst 164 and a lens with hazing in the center of the lens 165. Other configurations, mimicking visual anomalies can be placed on lenses to be held in the card 160. It is evident that the card 160 can be used with either the right eye or left eye simply by reversing the card.

It is clear that the benefits realized for the contact lenses herein above described are equally applicable to the eyeglass modifications, as for example, clip-on glasses, hinged visor to be attached to regular eyeglasses, loupes, slide behind lenses and modified press-on thin film.

It would be evident to those skilled in the art that the eyeglasses of this invention can be fashioned as wrap-arounds. In addition, the lens can be placed in front of the patient's eye during examination as a trial lens. Stick-on lens, it is clear, can be adhesive or simply adhering plastic. The stick-on lens can be just about the size of the opacity or optical zone we are portraying.

It is obvious that various degrees of hazing and combinations of hazing can be produced using the embodiments of this invention. For example, the eyeglass can have one or both lenses hazed. With the use of multiple hazed flip-up lenses, different degrees of hazing can be produced. The flip-up lenses can be fashioned so that the right and left lens move independently. The peel-ons can be applied to a single lens with a single peel-on or multiple peel-ons. In some instances, a single eyeglass will accommodate a different number of peel-ons depending on the degree of hazing desired. All of these combinations are designed to enable the patient to give the doctor more effective informed consent.

Advantageously, the modified contact lenses and eyeglass lenses of this invention can be of the patient's prescription.

Many advantages are envisioned by the use of the contact lenses of this invention. Primarily, the contact lenses when worn by the patient will simulate visual distortions that might be experienced postoperatively. Thus the informed consent from the patient after wearing the contact lenses will be more meaningful. This is so because the consent will be based on information derived from an objective physiological assessment, rather than a subjective verbal communication between doctor and patient. The use of contact lenses simulating postoperative visual defects may become the standard for legal informed consent in ophthalmologic surgery. Aside from being instructive to the patient, the contact lenses herein described are an educational aid. Student doctors, nurses and other interested parties, such as members of the family of a candidate for eye surgery could apply the contact lenses to objectively apprise themselves of possible postoperative visual deficiencies.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. A method of obtaining informed consent from a patient prior to ophthalmic surgery comprising having the prospective patient wear eyeglasses whose lens has been hazed so as to produce when worn an ophthalmological anomaly and then obtaining informed consent from said patent.

2. A contact lens useful in simulating an ophthalmologic anomaly which may be the post-operative result of surgery, comprising a contact lens whose surface has been modified by hazing to simulate said ophthalmologic anomaly.

3. A method of obtaining informed consent from a patient prior to ophthalmic surgery comprising having the prospective patient wear a contact lens with a hazed lens so as to produce when worn an ophthalmological anomaly and then obtaining informed consent from said patient.

4. A method of obtaining informed consent from a patient prior to ophthalmic surgery comprising having the prospective patient look through a lens provided in a card, said lens having been modified to produce when worn an ophthalmological anomaly and then obtaining informed consent from said patient.

* * * * *